United States Patent
Giordano et al.

(10) Patent No.: US 7,052,710 B2
(45) Date of Patent: *May 30, 2006

(54) POLYMER RE-INFORCED ANATOMICALLY ACCURATE BIOACTIVE PROTHESES

(75) Inventors: Russell A. Giordano, Marlborough, MA (US); Benjamin M. Wu, West Roxbury, MA (US)

(73) Assignee: Trustees of Boston University, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/615,466

(22) Filed: Jul. 8, 2003

(65) Prior Publication Data

US 2004/0024470 A1     Feb. 5, 2004

Related U.S. Application Data

(63) Continuation of application No. 09/574,146, filed on May 18, 2000, now Pat. No. 6,605,293.

(60) Provisional application No. 60/182,825, filed on Feb. 16, 2000, provisional application No. 60/135,009, filed on May 20, 1999.

(51) Int. Cl.
    *A61F 2/36*     (2006.01)
(52) U.S. Cl. ............ 424/423; 424/422; 424/423; 424/484
(58) Field of Classification Search ........... 424/422, 424/423, 484
    See application file for complete search history.

(56) References Cited

U.S. PATENT DOCUMENTS

| 3,713,860 | A | | 1/1973 | Auskern |
| 4,351,069 | A | * | 9/1982 | Ballintyn et al. ........ 623/23.36 |
| 4,722,870 | A | | 2/1988 | White |
| 5,591,453 | A | * | 1/1997 | Ducheyne et al. .......... 424/484 |
| 5,591,543 | A | * | 1/1997 | Peled et al. ................. 429/312 |
| 5,676,745 | A | * | 10/1997 | Kelly et al. ................. 424/422 |

* cited by examiner

*Primary Examiner*—Michael G. Hartley
*Assistant Examiner*—Micah-Paul Young
(74) *Attorney, Agent, or Firm*—Gauthier & Connors LLP

(57) ABSTRACT

Customized implants for use in reconstructive bone surgeries where anatomical accuracy and bone adaptation are important, such as plastic and craniomaxillofacial reconstructions. This implant comprises a porous surface layer and a tough inner core of interpenetrating phase composite. The porous surface layer enhances the biocompatibility, tissue ingrowth, and implant stability. The tough inner core improves the mechanical properties of the implant with a high fracture toughness and a low modulus. The anatomical accuracy of the implants will minimize the intra-operative manipulation required to maintain a stable host bone-implant interface.

18 Claims, 1 Drawing Sheet

POLYMER RE-INFORCED ANATOMICALLY ACCURATE BIOACTIVE PROTHESES

CROSS-REFERENCE TO RELATED APPLICATION(S)

This application is a Continuation and hereby claims benefit under 35 U.S.C. § 120 to the following applications: Ser. No. 09/574,146 filing date May 18, 2000 now U.S. Pat No. 6,605,293.

This application claims priority to U.S. Provisional Pat. Appln. Ser. No. 60/182,825 filed Feb. 16, 2000 and U.S. Provisional Pat. Appln. Ser. No. 60/135,009 filed May 20, 1999.

BACKGROUND OF THE INVENTION

Over 80,000 craniofacial reconstructions are performed annually in the United States. Although allograft and autograft tissues are the most commonly utilized graft materials, they have a failure rate ranging from 13–30%. Synthetic materials that can be produced in large quantities have been developed in numerous forms as alternatives to the traditional bone derived graft materials. Ceramic materials such as hydroxyapatite (HA), bioglasses, and tricalcium phosphate, and polymeric materials including polyethylene and silicone are available commercially in a wide variety of craniomaxillofacial procedures. All commercially available systems have at least one of the following shortcomings; 1) poor adaptation to recipient sites, 2) insufficient biological fixation, and 3) inadequate mechanical properties. The ability to manufacture implants that can simultaneously address all three problems is both commercially and medically significant.

Implants which do not match the unique anatomical constraints of the defect sites often require manual modification (grinding) of the implants, and/or the recipient bone. Additional modification is often necessary on the external surfaces to produce the appropriate facial contours. Although manual alteration can be trivial in some cases, extensive modifications are often necessary. Pre-fabricated elastomeric silicone implants adapt easily to the recipient sites, but they are generally characterized by soft tissue encapsulation, bone resorption, migration, and distortion (drooping). The latter problems are believed to be related to the lack of biological fixation, or tissue penetration into the implant surface. Porous implants allow tissue penetration, but their porous nature severely degrade their mechanical properties. This is particularly true for porous ceramics implants, which tend to break during extensive manual modifications. Dense ceramic materials typically have greater load bearing ability than their porous counterparts, but their excessive stiffness (high modulus) may induce stress shielding.

In summary all commercially available systems have at least one of the following shortcomings; 1) poor adaptation to recipient sites, 2) insufficient biological fixation, and 3) inadequate mechanical properties. Implants which can simultaneously address all three problems can be both commercially and medically significant.

BRIEF SUMMARY OF THE INVENTION

This invention embodies implants comprising a porous surface layer and a tough inner core of interpenetrating phase composite, offering several advantages over currently available implants utilized for the replacement or augmentation of the craniofacial bones. The porous surface layer enhances the biocompatibility, tissue ingrowth, and implant stability over commercially available polymer implants, while the tough inner core improves the mechanical properties of the implant by allowing for a higher fracture toughness and a lower modulus than commercially available ceramic implants. The anatomical accuracy of the implants will minimize the intra-operative manipulation required to maintain a stable host bone-implant interface, which is important in gaining surgeon and patient acceptance by reducing surgical time and enhancing the ability of porous surface layer to support bone formation.

Broadly the invention comprises implants having internal regions of high fracture toughness. The internal regions are one or more interpenetrating phases.

Anatomically shaped, porous preform are fabricated, and subjected to secondary post-processing steps depending on preform material and desired preform properties. The preform comprise continuous network of partially fused particles. Next, an inhibition layer is produced along desired surfaces of the preform by selectively coating the preform with a thin layer of fugitive material. The inner core of the preform is infused with a polymer precursor. The infused samples are processed to convert the precursor to a polymer, resulting in a interpenetrating phase composite in the inner core of the preform. Finally, the fugitive material is eliminated from the preform, leaving an open porous layer.

In a preferred embodiment, the phases are hydroxyapatite and polyethylene. Hydroxyapatite has been used extensively due to its chemical and crystallographic similarities to human bone minerals. With a flexural strength of 100 MPa, a fracture toughness ($K_{IC}$) of ~1 MPa m$^{1/2}$, and a modulus of ~100 GPa, hydroxyapatite per se is too brittle and stiff for applications other than coatings and non-weight bearing implants. For comparison, human femur has a flexural strength of 170 MPa, a modulus of 15 GPa, and a fracture toughness ($K_{IC}$) of 6.4 MPa m$^{1/2}$. The fracture toughness of human cortical bone has been reported to range from 2 to 12 MPa m$^{1/2}$. Numerous attempts have been made to toughen hydroxyapatite.

In this preferred embodiment, interpenetrating phase implants are produced by first fabricating a proper preform shape with hydroxyapatite powder, partially sintering the hydroxyapatite particles, and finally infusing the inter-particulate pores with the polymer. Because only slight sintering is necessary, near net-shape implants can be produced with minimal anisotropic shrinkage and non-uniform residual stress distribution that are often encountered during complete densification of complicated shapes. The surface porosity can be preserved for tissue ingrowth by first filling the surface pores with a temporary filling material prior to infusion, and removing the temporary material to reveal the surface pores. Many FDA-approved polymers can be utilized for the filling material, e.g. polyethylene glycol, waxes, hydrogels, acrylic latexes, and other water-soluble or water-dispersible materials.

One alternative embodiment of the invention comprises multiple infusion of polymer/monomer combinations to create an implant which contains a gradation of resorbable polymers such that the rate at which the polymers resorb varies across the implant.

Another alternative embodiment of the invention comprises infusion of active/monomer, active/polymer, active/monomer/polymer, active/polymer/monomer/inorganic combinations where the active can be selected from the group consisting of drug molecules, growth factors, adhesion peptides, promoters, activators and other regulators of gene expression.

Still another alternative embodiment of the invention comprises infusion of polymer/monomer combinations with inorganic material dispersed in the polymer/monomer mixtures. The inorganic matter can be resorbable glasses, silica, etc., which may aid in improving the mechanical properties of the device.

Still another alternative embodiment of the invention comprises infusion of polymer/monomer combinations with inorganic-precursors dispersed in the polymer/monomer combinations. Examples of inorganic precursors include but are not limited to alkoxides (metal alkoxides, silicon alkoxides, non-silicate tetravalent metal alkoxides, sol-gel organic-inorganic hybrids, and other organic-inorganic hybrids which can lead to in situ crystallization inside the preform, or formation of another interpenetrating phase organic-inorganic hybrid inside the preform.

DESCRIPTION OF THE PREFERRED EMBODIMENT(S)

Figure 1:
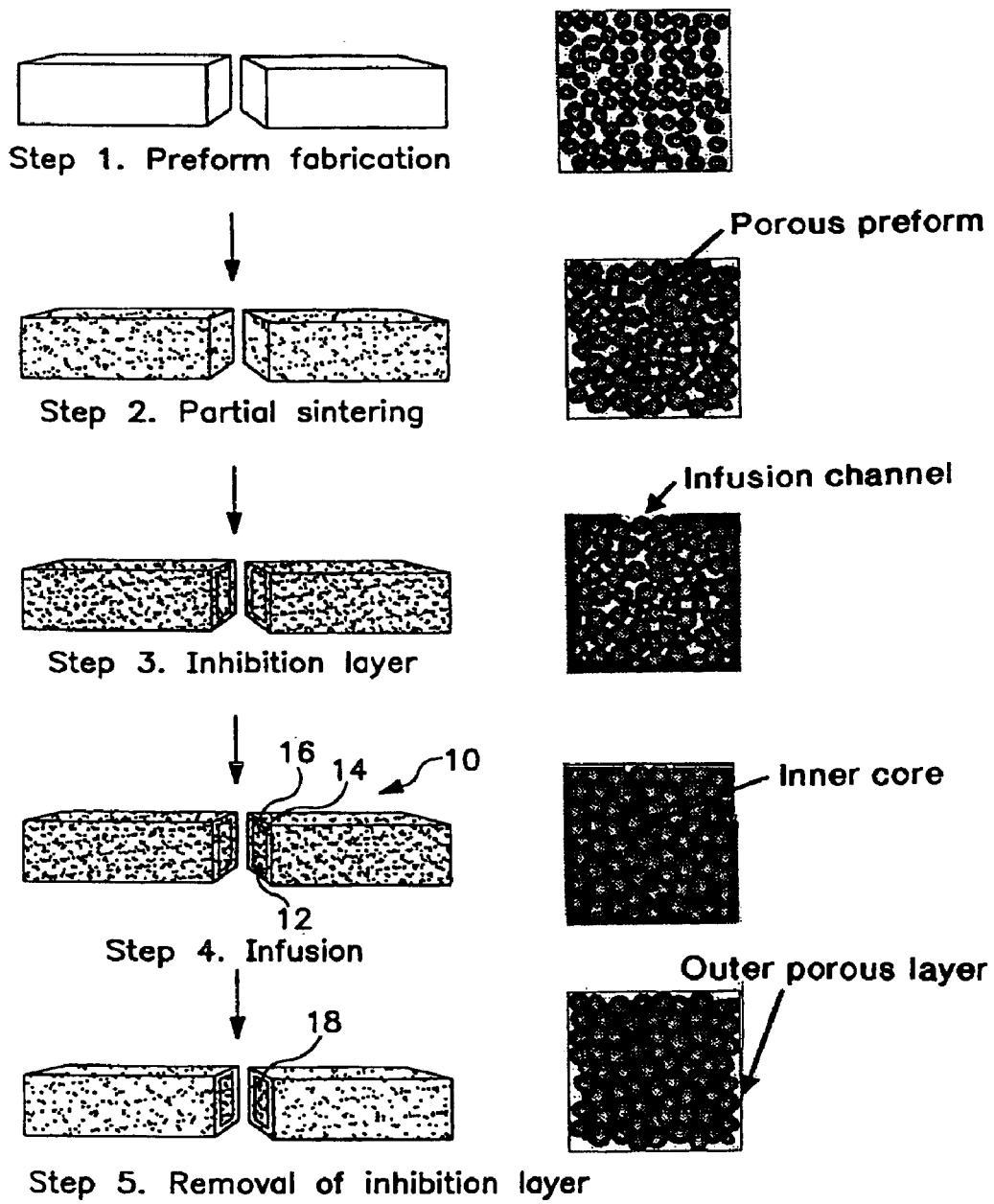
FIG. 1 is an illustration of the steps of a process of the invention.

The porous preform materials can be selected from, but not limited to hydroxyapatite, bioactive glass, calcium phosphates, xenografts, allografts, autografts, isografts, ultrahigh density zirconia, zirconia toughened alumina, alumina, sapphire, titanium, gold/palladium alloys.

The porous preform can be fabricated by numerous manufacturing routes. For off the shelf implants systems which offer standard sizes and shapes, many conventional processing techniques can be used, including, but not limited to injection molding, compression molding, blow molding, thermoforming, die pressing, slip casting, electrochemical machining, laser cutting, water-jet machining, electrophoretic deposition, powder injection molding, sand casting, shell mold casting, lost foam casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing spinning, and powder metallurgy compaction.

The implants can also be custom designed based on CAD models derived from medical imaging data such as MRI and CT scans, and computer driven manufacturing techniques such as, but not limited to computerized numerical controlled machining (CNC), electrodischarge maching (EDM), laminated object manufacturing (LOM), computer aided manufacturing of laminated engineering materials (CAM-LEM), stereolithography (SLA), selective laser sintering (SLS), and solid ground curing (SGC), fused deposition modeling (FDM), three dimensional printing (3DP), and Turbocasting. The preform can be made either directly by these CAD-based processes, or indirectly from non-functional templates made by these CAD-based processes. That is, numerous software packages are already available to convert common medical images into enhanced 3D renderings for pre-surgical visualization and planning. Depending on the file format, the rendering data can be used by service bureaus to fabricate life-size, reference prototype models to facilitate pre-surgical planning.

The porous preform, regardless of manufacturing route, are then subjected a series of post-processing steps.

Partial Sintering

A porous preform with approximately 20–50% residual interconnected porosity.

The actual sequence of post-processing steps depends on the preform material, fabrication technique and the desired implant properties. The first common post-processing step is controlled sintering, which also varies with the preform material. The partial sintering cycle for a common bioceramic, hydroxyapatite is described.

Complete sintering of hydroxyapatite (HA) to full density typically involves peak firing temperatures of 1250° C. to 1350° C. for approximately 4 hours in a moist atmosphere. Air firing predisposes the HA to decompose into tricalcium phosphate especially at temperatures above 1100° C. By sintering in a humid atmosphere, this decomposition can be prevented, even while sintering at 1300° C. Partial sintering will occur at approximately 1100° C., resulting in an interconnected open porous ceramic matrix which is 200° C. lower than the temperature required for full densification. Densification at a given temperature will, in part, be related to the initial powder particle size. Sintering involves several stages. Initially, adjacent particles connect at small areas called necks. As mass transport continues, pores become closed and decrease in size until full density is achieved. Neck growth between particles is dependent upon particle size, temperature, and sintering time. Essentially the low sintering temperature "freezes" the material in the initial stage of densification—interparticle necking. This results in minimal shrinkage (less than 5%), an open porosity, and an interconnected ceramic matrix. The actual amount of shrinkage depends on the green density, and the intra-particle porosity of the raw powder. The specimens are fired initially over a range of temperatures from 850° C. to 1350° C. in 100° C. intervals in a moist atmosphere. A tube furnace is used in order to easily control the atmospheric conditions by using a constant flow of humid air at rate of 0.01 to 0.5 m3h−1. The density at each sintering schedule (850° C. to 1350° C. in 100° C. intervals) is measured and the sintering schedule which produces the desirable density (50%–80%) and pore size distribution of 1 to 20 μm is used for all subsequent processing. Total porosity and pore size distribution of representative porous samples are characterized by mercury porosimetry. This information is useful in controlling desired porosity for the selected HA material and can be compared in the future with other materials.

Inhibition Layer

To preserve the surface porosity layer by inhibiting the infusing phase from filling the surface pores.

A fugitive material is infused to a depth ranging from 100–1000 microns. Infusion time can be used to control penetration depth. An approximation of infusion time and depth is made using the following equation which describes infusion velocity, vi, due to applied and capillary pressure: As noted in the equation, other variables can affect the infusion velocity, and hence the inhibition depth. Variables which are easily controllable are applied pressure, and resin viscosity.

$$v_i = [P_a(2R^2) + \gamma 8R \cos \phi]/32 \eta L$$

$P_a$=applied pressure
$R$=pore/capillary radius

γ=liquid/vapor surface energy
φ=contact angle
η=viscosity
L=capillary length

Suitable fugitive materials include but are not limited to polyethylene glycol, waxes, hydrogels, acrylic latexes, and other water-soluble or water-dispersible materials.

Selected portions of the surfaces are not covered with the inhibition layer. These areas serve as infusion channels for the infiltrating resin. Referring to FIG. 1, a section of an implant 10 is shown at step 4 comprising an inner core 12, an inhibition outer layer 14 and an infusion channel 14. At step 5, a porous outer layer 16 is shown. Specifically, formation of the inhibition layer is carried out as follows. Polyethylene glycol or polyethylene glycol/water solution is applied on the porous implant surfaces to form the desirable pattern, and if necessary, preserve an infusion channel. The implant is then placed in a furnace and heated to a temperature to cause the polyethylene glycol or polyethylene glycol solution to flow and infuse into the porous implant. The heating time determines the penetration distance. For example, heating treating at 60° C. for 1 hour allows the penetration depth of 500–1000 μm of a fugitive polymer, comprised of a 37.5 wt % solution of 35,000 MW polyethylene glycol in water, into a porous preform with an average pore size of 16 μm.

Infusion

To produce a tough inner core of interpenetrating phase composite

In the broadest aspect of the invention, the interpenetrating phase comprises two networks or material which are bound to one another. One network is the porous preform. The other inner core network is any material having a molecular lattice structure in the solid state. In the preferred embodiment, multiple infusion of the other inner core networks are used to precisely tailor the characteristics of the preform.

A tough inner core is produced by infusing the porous preform with a polymer precursor. Infusion is accomplished by using a vacuum chamber which is initially filled with sufficient precursor. Inside the chamber, the samples are secured in a sample holder which is suspended above the liquid. The entire chamber is evacuated until a constant minimum pressure of $10^{-4}$ to $10^{-2}$ torr is obtained. The evacuation time depends on the number and size of samples in the chamber. The samples are then lowered into the precursor, which will fill the internal pores via capillary action. The rate of infusion depends on materials properties such as contact angle, viscosity, pore size distribution, and pore volume. After complete infusion, the precursor is treated appropriately to result in polymerization without inducing excessive stresses in the porous preform.

Materials appropriate for infusion include, but not limited to:

Monomers (acrylates such as, but not limited to TEGDMA triethylene glycol dimethacrylate, MMA methyl methacrylate, Bis GMA 2,2-bis[4(2-hydroxy-3methacryloyloxy-propyloxy)-phenyl] propane); thermoplastics (such as, but not limited to styrene, vinyl acetate, vinyl chloride, polyethylene, PTFE potytetraflouroethylene, polypropylene); epoxies (polyetherketone, polyetheretherketone, polyphenylene oxide) resorbable polymers (such as, but not limited to polylactic acid, polyglycolic acid, polycaprolactone, polytrimethylene carbonate, polydioxanone, polyiminocarbonates, polyamides, polyorthoesters, polyanhydrides, polyhydroxyalkanoates, polyhydroxybutyrate); water soluble/hydrophilic (polyvinyl alcohol, PVA poly vinyl alcohol-based mixtures, collagen gel/poly (alpha hydroxyacids), cellulose, waxes; etc.

Thermosetting of monomers after infusion may be accomplished by adding a peroxide initiator such as, but not limited to benzoyl peroxide or an azo compound such as, but not limited to isobutylnitrile.

Accelerators or chemical initiators may also be used to enhance the setting reaction. An amine accelerating or initiating agent such as but not limited to triethanolamine, or dimethylaminoethyl methacryalate may be used.

Alternatively a photoinitiator may be used such as but not limited to camphorquinone.

Infusion of soluble or insoluble resins and polymers. The porous part, after external infusion with a soluble or low fusing polymer/monomer is treated with a coupling agent. The part is then placed in a chamber containing the desired individual polymer/monomer or mixture of polymer/monomers. The selected polymer/monomer is in a liquid state and the liquid is drawn into the pores via capillary action with or without the aid of pressure, vacuum, or a combination thereof. The liquid is then cured either by heat, light, chemical or combination thereof. Thermoplastics may be hardened by a decrease in infusion temperature.

Some combination of preform and polymer precursor may require the use of coupling agents to improve the wetting and hence the infusion. Coupling agents are, but not limited to silanes (such as but not limited amine, epoxy, chloroalkyl, mercapto, vinyl, styryl, aromatic, methacrylate, alkanolamine, and isocyanate); and titanates (such as, but not limited to the following classes: isopropyl, phosphate, styryl, amine, and acryl). Coupling agents can be diluted with an alcohol or ether/water mixture which is acidified using an acid such as, but not limited to acetic acid, hydrochloric, phosphoric, or sulfuric.

Removal of Inhibition Layer

To reveal the desired surface porosity.

The fugitive material comprising the inhibition layer are then removed by selective dissolution in the appropriate solvents, and/or thermal treatment, depending on the fugitive material. For the preferred fugitive material described in the section on Inhibition Layer, the removal of the layer is achieved by dissolving the fugitive material (polyethylene glycol) in water of a weak acid (acetic, etc.) solution.

Implant Features

The implants embodying the invention exhibit a) a porous outer layer, and b) an tough inner core which can contain selected porous regions or features. The implant shape is modified to include pre-tab holes and features that facilitate rigid fixation.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

The invention claimed is:

1. A method for forming an implant having an inner core and an outer layer which comprises:
   fabricating a preform with an open pore network, the network having an outer layer and an inner core;

coating at least a portion of the outer layer of the preform with a fugitive material to form an inhibition layer and leaving selected portions of the outer layer uncoated to thereby create at least one infusion channel;

infusing selected regions of the inner core with at least one infusing media;

forming an interpenetrating phase composite in the inner core; and forming a porous outer layer by removing the fugitive material from the outer layer.

2. The method of claim 1 wherein the preform is fabricated by sintering.

3. The method of claim 2 wherein the preform comprises a material selected from the group consisting of hydroxyapatite, bioactive glass, calcium phosphates, xenografts, allografts, autografts, isografts, ultrahigh density zirconia, zirconia toughened alumina, alumina, sapphire, titanium and gold/palladium alloys.

4. The method of claim 1 wherein the fugitive material is selected from the group consisting of polyethylene glycol, waxes, hydrogels, acrylic latexes, and other water-soluble or water-dispersible materials.

5. The method of claim 1 wherein the infusion media is selected from the group consisting of acrylates including TEGDMA, MMA, Bis GMA; thermoplastics including styrene, vinyl acetate, vinyl chloride, polyethylene, PTFE, polypropylene); epoxies (polyetherketone, polyetheretherketone, polyphenylene oxide); resorbable polymers including polylactic acid, polyglycolic acid, polycaprolactone, polytrimethylene carbonate, polydioxanone, polyiminocarbonates, polyamides, polyorthoesters, polyanhydrides, polyhydroxyalkanoates, polyhydroxybutyrate); water soluble/hydrophilics including polyvinyl alcohol, PVA-based mixtures, collagen gel/poly(alpha hydroxyacids, cellulose and waxes.

6. The method of claim 5 which comprises:
infusing the inner core with at least two infusion media.

7. The method of claim 5 which comprises:
infusing the inner core with an inorganic material selected from the group consisting of resorbable glasses and silica.

8. The method of claim 5 which comprises:
infusing the inner core with a material selected from the group consisting of drug molecules, growth factors, adhesion peptides, promotors and activators.

9. The method of claim 5 which comprises:
infusing the inner core with inorganic precursors selected from the group consisting of alkoxides, metal alkoxides, silicon alkoxides, non-silicate tetravalent metal alkoxides and sol-gel organic-inorganic hybrids.

10. An implant which comprises:
a preform with an open pore network, the preform having an inner core and an outer layer, the inner core infused with a polymer which forms an interpenetrating phase composite in the inner core, the preform characterized by a flexural strength, a modulus and a fracture toughness which generally matches that of a target bone host, and at least a portion of the outer layer characterized by a defined porosity.

11. The method of claim 10 which comprises:
removing the fugitive material.

12. The implant of claim 10 wherein the preform is comprised of a material selected from the group consisting of hydroxyapatite, bioactive glass, calcium phosphates, xenografts, allografts, autografts, isografts, ultrahigh density zirconia, zirconia toughened alumina, alumina, sapphire, titanium and gold/palladium alloys.

13. The implant of claim 10 wherein the fugitive material is selected from the group consisting of polyethylene glycol, waxes, hydrogels, acrylic latexes, and other water-soluble or water-dispersible materials.

14. The implant of claim 10 wherein the infusion media is selected from the group consisting of acrylates including TEGDMA, MMA, Bis GMA; thermoplastics including styrene, vinyl acetate, vinyl chloride, polyethylene, PTFE, polypropylene); epoxies (polyetherketone, polyetheretherketone, polyphenylene oxide); resorbable polymers including polylactic acid, polyglycolic acid, polycaprolactone, polytrimethylene carbonate, polydioxanone, polyiminocarbonates, polyamides, polyorthoesters, polyanhydrides, polyhydroxyalkanoates, polyhydroxybutyrate); water soluble/hydrophilics including polyvinyl alcohol, PVA-based mixtures, collagen gel/poly(alpha hydroxyacids, cellulose and waxes.

15. The implant of claim 10 wherein the inner core is infused with at least two infusion media.

16. The implant of claim 14 wherein the inner core is infused with an inorganic material selected from the group consisting of resoluble glasses and silica.

17. The implant of claim 14 wherein the inner core is infused with a material selected from the group consisting of drug molecules, growth factors, adhesion peptides, promotors and activators.

18. The implant of claim 14 wherein the inner core is infused with inorganic precursors selected from the group consisting of alkoxides, metal alkoxides, silicon alkoxides, non-silicate tetravalent metal alkoxides and sol-gel organic-inorganic hybrids.

* * * * *